United States Patent [19]
Olson et al.

[11] Patent Number: 6,015,711
[45] Date of Patent: Jan. 18, 2000

[54] SMOOTH MUSCLE 22α PROMOTER, GENE TRANSFER VECTORS CONTAINING THE SAME, AND METHOD OF USE OF THE SAME TO TARGET GENE EXPRESSION IN ARTERIAL SMOOTH MUSCLE CELLS

[75] Inventors: Eric N. Olson; Li Li, both of Dallas, Tex.; Joseph M. Miano, Milwaukee, Wis.

[73] Assignee: The Board of Regents of the University of Texas System, Austin, Tex.

[21] Appl. No.: 09/123,465

[22] Filed: Jul. 28, 1998

Related U.S. Application Data

[63] Continuation of application No. 08/555,723, Nov. 14, 1995, Pat. No. 5,837,534.

[51] Int. Cl.$^7$ ............................................. A61K 48/00
[52] U.S. Cl. .................. 435/375; 435/320.1; 514/44; 536/23.1; 536/23.5; 536/24.1; 536/24.5
[58] Field of Search ....................... 435/320.1; 536/23.1, 536/24.1, 24.5, 23.5; 514/44

[56] References Cited

U.S. PATENT DOCUMENTS

| | | | |
|---|---|---|---|
| 5,266,488 | 11/1993 | Ordahl et al. | 435/349 |
| 5,304,489 | 4/1994 | Rosen | 435/320.1 |
| 5,328,470 | 7/1994 | Nabel et al. | 604/101 |
| 5,352,595 | 10/1994 | Tapscott et al. | 435/6 |

FOREIGN PATENT DOCUMENTS

| | | |
|---|---|---|
| WO9306223 | 4/1993 | WIPO . |
| WO9511307 | 4/1995 | WIPO . |

OTHER PUBLICATIONS

Shanahan et al, *Circulation Research,* 73(1):193–204 (1993).
Lees–Miller et al, *J. Biol. Chem.,* 262(7):2988–2991 (1987).
Duband et al, *Differentiation,* 55:1–11 (1993).
Ayme–Southgate et al, *J. Cell Biol.,* 108:521–531 (1989).
Lees–Miller et al, *Biochem. J.,* 224:705–709 (1987).
Gimona et al, *Eur. J. Biochem.,* 205:1067–1075 (1992).
Applegate et al, *J. Biol. Chem.,* 269(14):10683–10690 (1994).
Thweatt et al, *Biochem. and Biophys. Res. Comm.,* 187(1):1–7 (1992).
Nishida et al, *Biochem. International,* 23(4):663–668 (1991).
Pearlstone et al, *J. Biol. Chem.,* 262(13):5985–5991 (1987).
Solway et al, *J. Biol. Chem.,* 270:13460–13469 (Jun. 2, 1995).
Genbank Accession No. L41154, May 1, 1995.
Genbank Accession No. L41161, May 2, 1995.
Genbank Accession No. L41169, May 2, 1995.
Genbank Accession No. L41170, May 2, 1995.
Miano et al, *Circulation,* 90(No. 4, Part 2):I–245, Abstract No. 1315 (Oct. 1994).
Li Li et al, "Expression of SM22α Correlates with the Development of Cardiovascular System During Mouse Embryogenesis", Abstract No. P73 and Poster, Scientific Conference on the Molecular, Cellular, and Functional Aspects of Cardiovascular Development, New Orleans, Louisiana (Mar. 23–26, 1995).
Hanley et al, *BioTechniques,* 10(1):56 (1991).
Chang et al, *Science,* Abstract, 267(5197):518–522 (1995).
Werner et al, *EMBO J.,* Abstract, 12(7):2635–2643 (1993).
Kemp et al, *Biochem. J.,* 310:1037–1043 (1995).
Nishida et al, *Gene,* 130:297–302 (1993).
Sambrook et al, "Molecular Cloning: A Laboratory Manual", 2nd Ed., CHS Press, pp. 8.46–8.47, 9.2–9.3 and 16.56–16.57 (1989).
Sessa et al, *J. of Biol. Chem.,* 267:15274–15276 (1992).
Simons et al, *Nature,* 359:67–70 (1992).
Miller et al, *FASEB J.,* 9:190–199 (1995).
Mossler et al, *Development,* 122:2415–2425 (1996).
Latimer et al. Highly conserved upstream regions of the alpha1–antitrypsin gene in two mouse species govern liver––specific expression by different mechanisms. Molecular and Cellular Biology 10:760–769, Jun. 1990.
Eck and Wilson. Gene based therapy. In Goodman and Gilman's The pharmacological basis of therapeutics, 9th edition. McGraw–Hill. New York, 1995.
Orkin and Motulsky. Report and recommendation of the panel to asses the NIH investment in research on gene therapy, Dec. 1995.
Solway et al. Structure and expression of a smooth muscle cell–specific gene, SM22alpha. Journal of Biological Chemistry 270:13460–13469, Jun. 1995.
Chang et al. Cytostatic gene therapy for vascular proliferative disorders with a constitutively active form of the retinablastoma gene product. Science 267: 518–522, Jan. 1995.
Yokoyama et al. Transcriptional control of the endogenous MYC protooncogene by antisense RNA. Proc. Natl. Acad. Sci. USA 84: 7363–7367, Nov. 1987.
Bennett et al. Inhibition of vasscular smooth muscle cell proliferation in veitro and in vivo by c–myc antisense oligodeoxynucleotides. Journal of Clinical Investigation 93:820–828, Feb. 1994.
Miller and Vile. Targeted vectors for gene therapy. FASEB Journal 9: 190–199, Feb. 1995.

*Primary Examiner*—Bruce R. Campell
*Assistant Examiner*—Richard Schnizer
*Attorney, Agent, or Firm*—Sughrue, Mion, Zinn, Macpeak & Seas, PLLC

[57] ABSTRACT

The present invention relates to isolated DNA molecules encoding the murine SM22α promoter, gene transfer vectors containing the same, and method of use of the same to target gene expression in arterial smooth muscle cells.

6 Claims, 6 Drawing Sheets

FIG. 1

```
GACACCGAAGCTACTCTCCTTCCAGTCCACAAACGACCAAGCCTTCTCTG              50
CCTCAACATGGCCAACAAGGGTCCATCCTACGGCATGAGCCGAGAAGTGC             100
         M  A  N  K  G  P  S  Y  G  M  S  R  E  V              14
AGTCCAAAATTGAGAAGAAGTATGACGAGGAGCTGGAGGAGCGACTAGTG             150
 Q  S  K  I  E  K  K  Y  D  E  E  L  E  E  R  L  V              31
GAGTGGATTGTAGTGCAGTGTGGCCCTGATGTAGGCCGCCCAGATCGTGG             200
  E  W  I  V  V  Q  C  G  P  D  V  G  R  P  D  R  G             48
GCGCCTGGGCTTCCAGGTGTGGCTGAAGAATGGTGTGATTCTGAGCAAAT             250
   R  L  G  F  Q  V  W  L  K  N  G  V  I  L  S  K              65
TGGTGAACAGCCTGTATCCTGAGGGATCGAAGCCAGTGAAGGTGCCTGAG             300
 L  V  N  S  L  Y  P  E  G  S  K  P  V  K  V  P  E              82
AACCCACCCTCCATGGTCTTTAAGCAGATGGAACAGGTGGCTCAATTCTT             350
  N  P  P  S  M  V  F  K  Q  M  E  Q  V  A  Q  F  L             99
GAAGGCAGCTGAAGATTATGGAGTCATCAAGACTGACATGTTCCAGACTG             400
   K  A  A  E  D  Y  G  V  I  K  T  D  M  F  Q  T             116
TTGACCTCTATGAAGGTAAGGATATGGCAGCAGTGCAGAGGACTCTAATG             450
 V  D  L  Y  E  G  K  D  M  A  A  V  Q  R  T  L  M             133
GCTTTGGGCAGTTTGGCTGTGACCAAAAACGATGGAAACTACCGTGGAGA             500
  A  L  G  S  L  A  V  T  K  N  D  G  N  Y  R  G  D            150
TCCCAACTGGTTTATGAAGAAAGCCCAGGAGCATAAGAGGGACTTCACAG             550
   P  N  W  F  M  K  K  A  Q  E  H  K  R  D  F  T             167
ACAGCCAACTGCAGGAGGGGAAGCACGTCATTGGCCTTCAAATGGGCAGC             600
 D  S  Q  L  Q  E  G  K  H  V  I  G  L  Q  M  G  S             194
AACAGAGGAGCCTCGCAGGCTGGCATGACAGGCTATGGGCGACCCCGGCA             650
  N  R  G  A  S  Q  A  G  M  T  G  Y  G  R  P  R  Q            201
GATCATCAGTTAGAAAGGGAAGGCCAGCCCTGAGCTGCAGCATCCTGCTT             700
   I  I  S  *                                                  204
AGCCTGCCTCACAAATGCCTATGTAGGTTCTTAGCCCTGACAGCTCTGAG             750
GTGTCACTGGGCAAAGATGACTGCACATGGGCAGCTCCCACCTATCCTTA             800
GCCTCAGCCCAGCATCTTACCCCAGAGCCACCACTGCCCTGGCCCCTGTT             850
CCCAAGCTGTACCCCCACCTCTACTGTTCCTCTCATCCTGGAGTAAGCAG             900
GGAGAAGTGGGCTGGGGTAGCCTGCTGTAGGCCAGCCCACTGTCCTTGAT             950
ATCGAATGTCCTTTGAAGGAGACCCAGCCCAGCCTCTACATCTTTTCCTG            1000
GAATATGTTTTTGGGTTGAAATTCAAAAAGGAAAAAGCAAATATATAA              1050
ATATATATATAAAAAAAAAAAAAAAAAA                                  1078
```

FIG. 2

```
SM22α-mouse    MANKGPSYGMSREVQSKIEKKYDEELEERLVEMIVVQCGPDVGRPDRGRL
SM22α-rat      ---------------------------------------M---------
SM22α-human    -----------------------------------I-------------
SM22α-chicken  -------A----D-------D----D---------A---SS--------

SM22α-mouse    GFQWLKNGVILSKLVNSLYPEGSKPVKVPENPPSMVFKQMEQVAQFLKA
SM22α-rat      -------------------------------------------------
SM22α-human    -------------------------D-----------------------
SM22α-chicken  ------IV--Q-------D------D-----I-DS--T-------I---

SM22α-mouse    AEDYGVIKTDMFQTVDLYEGKDMAAVQRTLMALGSLAVTKNDGNYRGDPN
SM22α-rat      -----------T-------F-----------V-----------------
SM22α-human    ---S-------F-------------------------H-----------
SM22α-chicken  ------V----F-A---------------V-------H-H---------

SM22α-mouse    WFMKKAQEHKRDFTDSQLQEGKHVIGLQMGSNRGASQAGMTGYGRPRQII
SM22α-rat      -------------E-----------------------------------
SM22α-human    -------------E--E--------------------------------
SM22α-chicken  -------E-SE---K---NI-----T-K------SYGP-----------

SM22α-mouse    S*
SM22α-rat      -
SM22α-human    -
SM22α-chicken  -
```

FIG. 4

```
-445                                              CTGCAGTCAA GACTAGTTCC CACCAACTCG

ATTTTAAAGC CTTGCAAGAA GGTGGCTTGT TTGTCCCCTTG CAGGTTCCTT TGTCGGGCCA

AACTCTAGAA TGCCTCCCCC TTTCTTTCTC ATTGAAGAGC AGACCCAAGT CCGGGTAACA

AGGAAGGGTT TCAGGTCCT GCCCATAAAA GGTTTTTCCC GCCGCCCCTC AGCACCGCCC
                                  cArG

CGCCCCGACC CCCGCAGCAT CTCCAAAGCA TGCAGAGAAT GTCTCCCGGCT GCCCCCGACA
                                         cArG                          Sp1

GACTGCTCCA ACTTGGTGTC TTTCCCAAAT ATGGAGCCT GTGTGGAGTG AGTGGGGCGG
                                 TATA
CCCGGGGTGG TGAGCCAAGC AGACTTCCAT GGGCAGGGAG GGGCGCCAGC GGACGGCAGA
                                                                          +1
GGGGTGACAT CACTGCCTAG GCGGCCTTTA AACCCCTCAC CCAGCCGGCG CCCCAGCCCG
           *

TCTGCCCCAG CCCAGACACC GAAGCTACTC TCCTTCCAGT CCACAAACGA CCAAGCCTT
```

SMOOTH MUSCLE 22α PROMOTER, GENE TRANSFER VECTORS CONTAINING THE SAME, AND METHOD OF USE OF THE SAME TO TARGET GENE EXPRESSION IN ARTERIAL SMOOTH MUSCLE CELLS

This is a Continuation of U.S. patent application Ser. No. 08/555,723, U.S. Pat. No. 5,837,534 Nov. 17, 1998 filed Nov. 14, 1995 (now allowed).

This invention was developed in part under funding from the National Institutes of Health Grant No. AR-39849-07. The government has certain rights to this invention.

FIELD OF THE INVENTION

The present invention relates to isolated DNA molecules encoding the murine smooth muscle 22α (hereinafter "SM22α") promoter, gene transfer vectors containing the same, and method of use of the same to target gene expression in arterial smooth muscle cells.

BACKGROUND OF THE INVENTION

I. Muscle Cells

The three muscle cell types, skeletal, cardiac, and smooth, are each derived from distinct populations of myogenic precursor cells during embryogenesis (Christ et al, *Anat. Embryol.*, 191:381–396 (1995); and Schwartz et al, *Physiol. Rev.*, 70:1177–1209 (1990)).

Skeletal muscle arises from the somites, which form adjacent to the neural tube beginning at about embryonic day 8 (E8) in mice. Subsequent compartmentalization of the somites gives rise to the myotome, from which the axial musculature is derived (Buckingham, *Trends Genet.*, 8:144–148 (1992)). Cells from the ventrolateral edge of the dermamyotome of the somite also migrate into the limb buds to form the limb muscles (Buckingham, supra).

Cardiac muscle is derived from the anterior lateral plate mesoderm, which forms a primitive heart tube at about E8, and subsequently undergoes looping and chamber specification to form the mature multi-chambered heart (Kaufman, *The Atlas of Mouse Development*, Academic Press, San Diego (1992)).

The embryonic origins of smooth muscle cells (SMCS) are less clear, in part because they arise in multiple regions of the embryo from different precursor populations. For example, studies in chick/quail chimeras have shown that SMCs in the great vessels are derived from a subpopulation of mesenchymal neural crest cells, whereas SMCs in the coronary arteries are of non-neural crest origin (Hood et al, *Anat. Rec.*, 234:291–300 (1992); Rosenquist et al, *Ann. NY Acad. Sci.*, 588:106–119 (1990); Kirby et al, *Science*, 220:1059–1061 (1983); and Le Lièvre et al, *J. Embryol. Exp. Morphol.* 34:125–154 (1975)).

In addition to vascular SMC, there exists several seemingly distinct populations of SMC in most visceral organs, i.e., those of the respiratory, gastrointestinal and genitourinary systems. The visceral SMCs are thought to originate from local mesenchyme, apparently through inductive processes (Cunha et al, *Epith. Cell Biol.*, 1:76–83 (1992)).

II. Properties of Smooth Muscle Cells

SMCs are important for the functions of the circulatory, genito-urinary, respiratory and digestive systems. Unlike skeletal and cardiac muscle cells, where cell differentiation is accompanied by stable expression of muscle-specific genes (Weintraub et al, *Science*, 251:761–766 (1991); and Olson, *Genes Dev.*, 4:1454–1461 (1992)), SMCs display remarkable phenotypic plasticity, and retain the capacity to re-enter the cell cycle (Schwartz et al, *Circ. Res.*, 58:427–444 (1986)). This unique property of SMC phenotypic modulation is often associated with the loss of many SMC-specific markers (Glukhova et al, *Am. J. Physiol.*, 261:78–80 (1991); and Frid et al, *Dev. Biol.*, 153:185–193 (1992)). Such alterations in SMC proliferation and differentiation are associated with a variety of vascular diseases including atherosclerosis, restenosis following angioplasty, and hypertension (Schwartz et al (1986), supra; and Glukhova et al, supra).

From the above, it is clear that smooth muscle shows unique properties in terms of both differentiation control and ontogeny when compared to sarcomeric muscle.

In contrast to skeletal and cardiac muscle cells, where the molecular mechanisms governing muscle-specific gene expression are beginning to be understood (Olson, *Circ. Res.*, 72:1–6 (1993)), relatively little is known about the mechanisms controlling muscle gene expression in SMCs. Further, relatively little is known about the molecular mechanisms that control the SMC myogenic program, which are believed to be important for developing therapeutic strategies for the treatment of human vascular diseases.

Only a few SMC-specific marker genes, i.e., that are expressed specifically in adult SMCs, have been studied extensively in vitro with respect to transcriptional regulation. However, no in vivo studies have been carried out. Among these genes are smooth muscle (SM) α-actin (Foster et al, *J. Biol. Chem.*, 267:11995–12003 (1992); and Shimizu et al, *J. Biol. Chem.*, 270:7631–7643 (1995)), and smooth muscle myosin heavy chain (SM-MHC) (Katoh et al, *J. Biol. Chem.*, 269:30538–30545 (1994)). Another gene, SM22α has been less well characterized (Duband et al, *Differentiation*, 55:1–11 (1993); Nishida et al, *Gene*, 130:297–302 (1993); Shanahan et al, *Circ. Res.*, 73:193–204 (1993)); and Lees-Miller et al, *Biochem. J.*, 244:705–709 (1987)).

III. SM22α

SM22α is considered to be a SMC-specific protein structurally related to calponin, which is an actin- and tropomyosin-binding protein (Winder et al, *Adv. Exp. Med. Biol.*, 304:37–51 (1991)). SM22α also shows homology to the Drosophila protein mp20, which is expressed specifically in synchronous oscillatory flight muscles, but not in asynchronous flight muscles (Ayme-Southgate et al, *J. Cell Biol.*, 108:521–531 (1989)). In addition, SM22α shows homology to protein NP25, which is expressed specifically in a subpopulation of neuronal cells (Ren et al, *Mol. Brain Res.*, 22:173–185 (1994)).

There are three isoforms of SM22α, but the α-isoform is the most abundant one (Lees-Miller et al, supra; and Lees-Miller et al, *J. Biol. Chem.*, 262:2988–2993 (1987)).

SM22α has been shown to be expressed in all smooth muscle tissues of birds and mammals. However, SM22α mRNA expression during embryogenesis has not been examined. Thus, to begin to define the mechanisms that control muscle gene expression during SMC differentiation, and to further characterize the embryonic origins of SMC lineages, the murine SM22α gene was cloned in the present invention, and its mRNA expression pattern examined during murine embryogenesis.

IV. Targeted Gene Therapy

Several reports have described the use of adenoviral or liposome-mediated gene transfer in the vessel wall to potentially treat vascular diseases that account for more annual deaths than all cancers combined. These reports have relied on constitutively active DNA viral promoters or liposomes to direct expression of foreign DNA in SMCs (Nabel et al, *Science*, 249:1258–1288 (1990); Stewart et al, *Hum. Gene*

Therapy, 3:267–275 (1992); Nabel et al, Nature, 362:844–846 (1993); and Chang et al, Science, 267:518–522 (1995)). Despite successful transfer of a number of recombinant proteins that can influence the biology of SMC in vivo, these previously known gene transfer vectors do not assure SMC specificity. That is, the transfected DNA is taken up by other vascular cells, especially the vessel lining endothelial cells.

Accordingly, there has been a desire in the art isolate SMC-specific promoters so as to develop a gene transfer vector system that can deliver genes specifically expressible in the SMC of the vasculature. The development of a gene transfer vector system that can specifically direct the expression of foreign genes in SMCs would represent an important step toward developing therapeutic strategies for treatment of human vascular diseases. In particular, restenosis of the vascular wall, which is a major complication following angioplasty to eliminate vascular occlusions during atherosclerosis.

The SM22α promoter isolated in the present invention is active only in vascular SMC of large arteries and immediate branches, i.e., no activity is seen in SMCs of veins, small arteries and visceral organs. The absence of visceral SMC activity indicates that a separable control element(s) governs SM22α in these tissues, thus making the promoter of the present invention well-suited for gene therapy of the arterial vessel wall, i.e., no leaky expression would be expected in such tissues as veins, small arteries, stomach, intestine, lung and bladder. The SM22α promoter is the only arterial SMC-specific gene control region identified to date. It therefore, represents a powerful means of directing the selective expression of foreign genes within SMCs in the vasculature, which can be delivered by gene transfer vectors.

SUMMARY OF THE INVENTION

An object of the present invention is to provide an isolated DNA molecule encoding the SM22α promoter.

Another object of the present invention is to provide gene transfer vectors containing the SM22α promoter.

Still another object of the present invention is to provide a method for targeting foreign gene expression in arterial SMCs in vitro and in vivo.

Another object of the present invention is to provide a transgenic mouse harboring the lacZ transgene driven by the SM22α promoter, which can be used to examine the effect of other genes or drugs on the cardiovascular system.

These and other objects of the present invention, which will be apparent from the detailed description of the invention provided hereinafter, have been met, in one embodiment, by inter alia, an isolated DNA molecule having a nucleotide sequence selected from the group consisting of SEQ NO:3, SEQ ID NO:4, SEQ ID NO:5 and SEQ ID NO:6.

BRIEF DESCRIPTION OF THE DRAWINGS

FIG. 1 shows the nucleotide sequence of murine SM22α cDNA (SEQ ID NO:1), and the deduced open reading frame of the murine SM22α protein (SEQ ID NO:2).

FIG. 2 shows homology between the amino acid sequences of SM22α proteins from mice, rats, humans and chickens. A dash indicates amino acid identity at that position.

FIG. 4 shows the nucleotide sequence of the transcription unit and 5' flanking region of the SM22α gene (SEQ ID NO:6). Nucleotides are numbered relative to the transcription initiation site (designated as +1). The first exon is underlined. CArG boxes and Sp1 sites are indicated. –445 represents the 5' end of the promoter fragment in the plasmid pSM445-luc. The asterisk above nucleotide +20 designates the end of the SM22α cDNA sequence. The potential TATA-like element is located at –28 to –24.

DETAILED DESCRIPTION OF THE INVENTION

Figure 3:
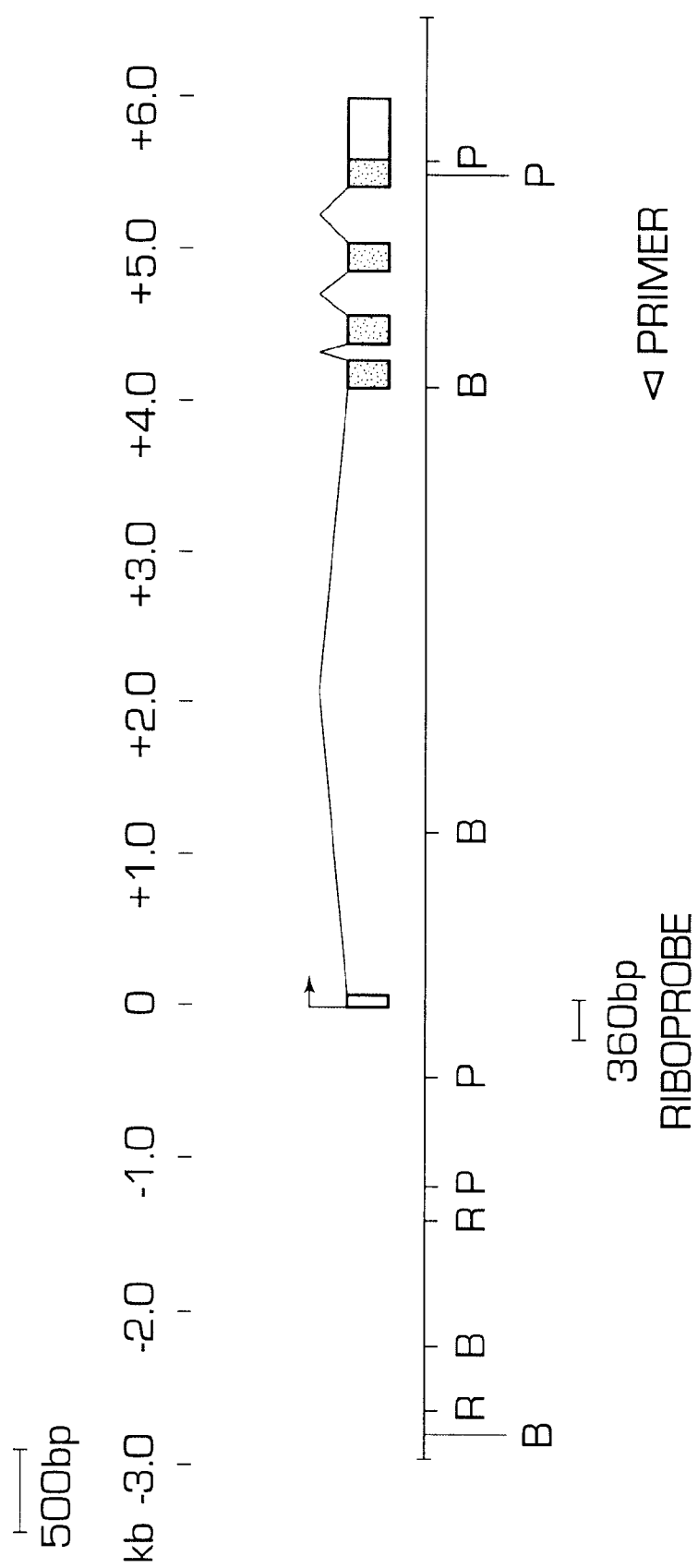
FIG. 3 shows the intron/exon organization of SM22α determined by sequence comparison between SM22α genomic DNA and SM22α cDNA, and by PCR using primers from the cDNA sequence. The intron-exon boundaries are consistent with the splicing consensus. Exons are indicated by boxes; the black box denotes the coding sequence, and the white box denotes the noncoding sequence. The arrow indicates the transcription initiation site. A restriction map of the SM22α genomic clone is shown below the schematic of the gene. In the restriction map, B=BalI; P=PstI; and R=EcoRI. The position of the primer used for primer extension is indicated by an arrowhead beneath the genomic map. The 3' end of the primer corresponds to nucleotide 131 of the SM22α cDNA. The position of a 360 bp riboprobe used in RNase protection assays to map the transcription start site is also indicated.

As discussed above, in one embodiment, the above described objects of the present invention have been met by, inter alia, an isolated DNA molecule having a nucleotide sequence selected from the group consisting of SEQ NO:3, SEQ ID NO:4, SEQ ID NO:5 and SEQ ID NO:6, and a gene transfer vector comprising said DNA molecule operably linked to foreign DNA.

As used herein, the expression "foreign DNA" refers to DNA encoding for a polypeptide or RNA that is not naturally under the control of the SM22α promoter. Thus, foreign DNA can be DNA which encodes for any polypeptide or RNA important for cardiovascular development other than SM22α. However, in addition to the foreign DNA, the SM22α promoter can also be used to express the SM22α protein in situations where, because of, e.g., a genetic defect, there is insufficient production of this protein in the host.

The particular polypeptide is not critical to the present invention, and is generally a polypeptide encoding a gene product useful in the treatment of vascular diseases. Examples of such polypeptides include basic fibroblast growth factor receptor 1 dominant negative mutant (Werner et al, EMBO J., 12:2635–2643 (1993)), p21 (El-Deiry et al, Cancer Research, 55:2910–2919 (1995)), angiopeptin (Foegh et al, J. Vasc. Sur., 19(6):1084–1091 (1994)), endothelial cell nitric oxide synthase (Sessa et al, J. Biol. Chem., 267:15274 (1992)), and non-phosphorylated Rb (Chang et al, Science, 267:518–522 (1995)).

The polypeptide can also encode multimerized DNA binding sites for transcription factors, and is generally any DNA binding site for transcription factors involved in SMC proliferation, and thus useful in the treatment of vascular diseases. The particular multimerized binding sites for transcription factors is not critical to the present invention. Examples of such DNA binding sites include the E2F binding site (Morishita et al, *Proc. Natl. Acad. Sci., USA*, 92:5855–5859 (1995)).

The particular RNA is not critical to the present invention, and is generally any RNA useful in the treatment of vascular diseases. Examples of such RNAs include anti-sense c-myc RNA (Edelman et al, *Cir. Res.*, 76:176–182 (1995)), and anti-sense c-myb RNA (Simons et al, *Nature*, 359:67–70 (1992)).

The gene transfer vector of the present invention may additionally comprise a gene encoding a marker or reporter molecule to more easily trace expression of the vector.

The particular reporter molecule which can be employed in the present invention is not critical thereto. Examples of such reporter molecules which can be employed in the present invention are well-known in the art and include β-galactosidase (Fowler et al, *Proc. Natl. Acad. Sci., USA*, 74:1507 (1977)), luciferase (Tu et al, *Biochem.*, 14:1970 (1975)), and chloramphenicol acetyltransferase (Gorman et al, *Mol. Cell Biol.*, 2:1044–1051 (1982)).

The gene transfer vector may contain more than one gene encoding the same or different foreign polypeptides or RNAs.

The particular gene transfer vector employed is not critical to the present invention. The gene transfer vector may be any construct which is able to replicate within a host cell and includes plasmids, DNA viruses, retroviruses, as well as isolated nucleotide molecules. Liposome-mediated transfer of the gene transfer vector may also be carried out in the present invention.

The particular plasmid employed is not critical to the present invention. Examples of such plasmids which can be employed in the present invention include pGL3-based plasmids (Promega).

The particular DNA virus employed is not critical to the present invention. Example of such DNA viruses which can be employed in the present invention are adenoviruses.

Adenoviruses have attracted increasing attention as expression vectors, especially for human gene therapy (Berkner, *Curr. Top. Microbiol. Immunol.*, 158:39–66 (1992)).

The particular adenovirus serotype employed in the present invention is not critical. Examples of such adenovirus serotypes which can be employed in the present invention are well-known in the art and include more than 40 different human adenoviruses, e.g., Ad12 (subgenus A), Ad3 and Ad7 (Subgenus B), Ad2 and Ad5 (Subgenus C), Ad8 (Subgenus D), Ad4 (Subgenus E), Ad40 (Subgenus F) (Wigand et al, *In: Adenovirus DNA*, Doerfler, Ed., Martinus Nijhoff Publishing, Boston, pp. 408–441 (1986)). Ad5 of subgroup C is the preferred adenovirus employed in the present invention. This is because Ad5 is a human adenovirus about which a great deal of biochemical and genetic information is known, and it has historically been used for most constructions employing adenovirus as a vector. Also, adenoviral vectors are commercially available, e.g., pCA3 (Microbix Biosystems Inc.).

Methods for producing adenovirus vectors are well-known in the art (Berkner et al, *Nucleic Acids Res.*, 11:6003–6020 (1983); van Doren et al, *Mol. Cell. Biol.*, 4:1653–1656 (1984); Ghosh-Choudhury et al, *Biochem. Biophys. Res. Commun.*, 147:964–973 (1987); McGrory et al, *Virol.*, 163:614–617 (1988); and Gluzman et al, *In: Eurkaryotic Viral Vectors*, Ed. Gluzman, Y. pages 187–192, Cold Spring Harbor Laboratory (1982)).

The transgenic animals of the present invention harbor the SM22α promoter operable in cells, and the foreign DNA includes a region coding for a ribosomal binding site operable in cells.

The method for producing the transgenic animals of the present invention is not critical. The transgenic animals can be produced by infecting the animals, e.g., embryo, juvenile or adult animals, with a gene transfer vector in the form of a DNA virus. Alternatively, transgenic animals may be produced by microinjecting the gene transfer vectors of the present invention into animals oocysts, eggs, and embryos as described by Old et al, *Principles of Gene Manipulation*, 3rd Ed., pages 225–271 (1985).

The multiplicity of infection is not critical to the present invention. Generally the multiplicity of infection of the adenovirus vectors will be in the range of about 1 to 100, preferably in the range of about 1 to 10.

Infection can be carried out in vitro or in vivo. In vitro infection of cells is performed by adding the gene transfer vectors to the cell culture medium. When infection is carried out in vivo, the solution containing the gene transfer vectors may be administered by a variety of modes, depending on the tissue which is to be infected. Examples of such modes of administration include injection of gene transfer vectors into the arterial or venous vascular system, injection of gene transfer vectors directly into smooth muscle tissue, direct application to a surface of smooth muscle, or instillation into an organ (e.g., into the femoral artery by a Fogarty 2F double balloon catheter).

A transgenic mouse harboring the lacZ transgene driven by the SM22α promoter can be used to examine the effect of other genes or drugs on the cardiovascular system. For example, fibroblast growth factor (FGF) has been shown to affect smooth muscle proliferation in vivo. However, the role of FGF in cardiovascular development has not yet been determined. Thus, introduction of the gene encoding FGF into mouse embryos under the control of the SM22α promoter will give some insight into the importance of FGF in smooth muscle cell proliferation. In the resulting transgenic mouse, drugs designed to block the FGF signal transducing pathway can then be administered so as to examine their effects on SMC proliferation.

The following examples are provided for illustrative purposes only and are in no way intended to limit the scope of the present invention.

EXAMPLE 1

Isolation of Murine SM22α cDNA and Genomic Clones

A. Isolation of Murine SM22α cDNA

To study the regulation of SM22α gene expression no during murine development, first a murine SM22α cDNA of 1078 bp in length was isolated using sequences derived from rat SM22α cDNA.

More specifically, PCR was carried out on a murine uterus cDNA library (Miano et al, *Circ. Res.*, 75:803–812 (1994)) using the following forward primer and reverse primer, which correspond to nucleotides 1–21 and nucleotides 255–275, respectively, of the rat SM22α cDNA sequence (Nishida et al, *Gene*, 130:297–302 (1993)):

5'-ATGGCCAACAAGGGTCCATCC-3' (SEQ ID NO:7)

5'-TCCATCTGCTTGAAGACCATG-3' (SEQ ID NO:8).

The resulting 275 bp murine SM22α PCR fragment was subcloned into the EcoRI/HindIII sites of pBluescript SK+ (Stratagene; La Jolla, Calif.), and utilized for further library screening as discussed below, as well as in the RNase protection assays described in Example 2 below, and in the in situ hybridizations described in Example 3 below.

Using this 275 bp DNA fragment as a probe, several overlapping cDNA clones were isolated from the same uterus library under high stringency conditions, i.e., 50% (v/v) formamide was used for hybridization at 42° C. One clone, designated SM22α-cDNA (1.1 kb), was found to contain a 1078 bp insert. Both strands of clone SM22α-cDNA (1.1 kb) were sequenced by dideoxy sequencing using Sequenase (United States Biochemical) according to the manufacturer's instructions. The resulting nucleotide sequence (SEQ ID NO:1) including deduced amino acid sequence containing 201 amino acids open reading frame (SEQ ID NO:2) are shown in FIG. 1.

The SM22α mRNA transcript was found to be about 1.1 kb in length by Northern analysis. Thus, it appeared that the clone SM22α-cDNA (1.1 kb), containing 1078 bp, was nearly full-length.

Sequence analysis of the resulting deduced amino acid sequence versus that for the rat, humans and chicken SM22α proteins, was carried out using the GCG sequence analysis software package (Department of Biomathematics, University of Texas, M.D. Anderson Cancer Center). The sequence accession numbers at Genbank for rat SM22α, human SM22α and chicken SM22α proteins are M83107, M83106 and M83105, respectively.

The sequence analysis showed that the murine SM22α protein (see FIG. 1) shares 98%, 97%, and 84% identity with the rat, human, and chicken SM22α proteins, respectively (FIG. 2).

B. Isolation of Murine SM22α Genomic DNA

A murine SM22α genomic clone was isolated by screening the SV129 murine genomic phage library (Stratagene; La Jolla, Calif.) with the 1078 bp murine SM22α cDNA as a probe.

Screening of the murine SV129 genomic phage library was carried out by hybridizing DNA from the phage library on duplicate filters overnight at 42° C. in 50% (v/v) formamide in 5×SSC-5×Denhardt's solution comprising 0.05 M Na$_2$HPO$_4$ (pH 7.0), 0.1% (w/v) SDS and 100 μg/ml of salmon sperm DNA, using $^{32}$P-labelled SM22α cDNA from clone SM22α-cDNA (1.1 kb) as the probe. After washing in 1×SSC containing 0.1% (w/v) SDS, positive plaques were subjected to three successive rounds of screening.

One genomic clone, containing a 20 kb SM22α genomic DNA insert, was identified. The insert was excised from this clone by digestion with NotI, and subcloned into pBluescript SKII+ (Stratagene; La Jolla, Calif.) for further analysis. The resulting clone, designated as SM22α-20 kb/BSKII+, was deposited at the American Type Culture Collection on Nov. 13, 1995, under ATCC No. 97336. Southern analysis showed the same restriction maps for the isolated SM22α genomic DNA and SV129 genomic DNA, indicating that genomic clone SM22α-22 kb/BSKII+ was not rearranged.

EXAMPLE 2

RNase Protection Analysis

The pattern of SM22α mRNA expression in adult murine tissues was determined by a RNase protection assay.

A. Adult Murine Tissues

More specifically, total RNA from various murine tissues was isolated using the acid phenol protocol described by Chomczynski et al, *Anal. Biochem.*, 162:156–159 (1987). Approximately 15 μg of the total RNA was hybridized to an in vitro transcribed SM22α protected fragment "riboprobe" (~1.0×10$^5$ cpm) corresponding to the 275 bp PCR product described in Example 1 above, using the Maxi-Script and RPA kits (Ambion; Austin, Tex.). Hybridizations were carried out at 45° C. for 16 hr. Following hybridization, the samples were treated with RNase A+T for 40 min at 37° C., precipitated with ethanol, and resolved in a denaturing 5.0% (w/v) polyacrylamide gel containing 7.0% (w/v) urea. After soaking in 10% (v/v) acetic acid in 10% (v/v) methanol, the gel was vacuum dried, and exposed to autoradiographic film. These hybridizations included a 108 bp 18S rRNA riboprobe (Ambion) as a control.

SM22α mRNA transcripts were found to be present at the highest levels in the aorta, intestine, stomach, and uterus, which contain a large smooth muscle component. SM22α mRNA transcripts were detected at a lower level in the lung, kidney, spleen, brain, heart, and skeletal muscle. It is believed that expression in these tissues reflects the presence therein of vascular smooth muscle. SM22α mRNA transcripts were not detected in the liver and testes.

B. Cell Lines

Total RNA was isolated from various cell lines and tested in the same manner as discussed above, except that these hybridizations included a 156 bp riboprobe corresponding to the 3'-untranslated region of murine SM α-actin (Min et al, *Nucleic Acids Res.*, 16:10374 (1988)) as a control. RNA from the stomach was also included for positive control in this set of experiments. The conditions for differentiation of each cell line employed was as described by Miano et al, supra.

Although SM22α expression was found to be restricted to SMCs in adult murine tissues, SM22α mRNA transcripts were detected in cell lines derived from different origins, including the 10T1/2 (ATCC No. CCL 226) and 3T3 fibroblast cell lines (ATCC No. CCL 163), the BC3H1 muscle cell line, which has properties of smooth and skeletal muscle (Schubert et al, *J. Cell Biol.*, 61:398–413 (1974); and Edmondson et al, *Genes Dev.*, 3:628–640 (1989)), the C2 skeletal muscle cell line (ATCC No. CRL 1772), and the P19 embryonal carcinoma cell line (ATCC No. CRL 1825). However, no expression was detected in the F9 teratocarcinoma cell line (ATCC No. CRL 1720). In the BC3H1, C2, and P19 cell lines, no difference in expression in differentiated or undifferentiated cells was observed.

Thus, the SM22α transcripts were present in several non-SMC lines, as well as in SMC cell lines.

EXAMPLE 3

In situ Hybridization

A. SM22α Expression in Adult Tissue

To determine whether the expression of SM22α in adult skeletal and cardiac muscle found in Example 2 above was due to the presence of blood vessels in these tissues, sections of heart and skeletal muscle from 8 week-old mice were examined by in situ hybridization with an SM22α anti-sense riboprobe.

More specifically, the same 275 bp murine anti-sense probe utilized for RNase protection assays described in Example 2 above, was used for in situ hybridization, which was carried out as described by Miano et al, supra. Both sense and anti-sense probes were labeled with $^{35}$S-UTP, and hybridized to paraffin sections (8.0 μm) from staged embryos (7.5 days post-conception (dpc) to 17.5 dpc).

SM22α mRNA was not detected in the myocardium or in skeletal muscles, but instead was localized to the blood vessels present in these sections. Within the uterus, SM22α was highly expressed in the myometrial layer, with little or no expression in the glandular endometrial layer.

Thus, SM22α mRNA expression is highly restricted to adult smooth muscle, making it an excellent marker for studying the regulation of SMC differentiation.

B. SM22α Expression in Embryonic Tissue

To determine whether SM22α expression marks the smooth muscle lineage during embryogenesis, the expression of SM22α RNA transcripts was examined by in situ hybridization of murine embryos beginning at E7.5, in the same manner as described above for the adult tissue.

SM22α was found to be specifically expressed in adult SMCs, not in the heart. Surprisingly, SM22α RNA transcripts were first detected at E8.0 in the premyocardial tissue of the primitive heart tube. The primitive heart originates from the anterior portions of paired tubes derived from the splanchnic mesderm (Sadler, *Langman's Medical Embryology*, Williams & Wilkins, 5th Ed., Baltimore (1985)). No SM22α expression was detected elsewhere in the embryo at this stage, including the dorsal aorta.

At E8.5, the heart is asymmetric and contains a common atrium and ventricle in direct continuity with the aortic sac. At this stage, SM22α expression was observed throughout the bulbus cordis (the future right ventricle), and the newly formed common ventricle of the primitive heart. At E8.5, SM22α expression increased in the heart. High-level expression was also observed in the aortic sac at this stage.

Between E9.5–10.5, the volume of the heart increases dramatically, the outflow tract begins to differentiate, and the aortic arches are formed. SM22α continued to be expressed at high levels throughout the entire developing heart and the outflow tract until E10.5. SM22α expression gradually diminished in the heart after E10.5. By E12.5, expression was restricted to the right ventricle, and it became undetectable in the heart by E13.5.

SM22α expression was also observed in the myotomal compartment of the somites beginning at E9.5. Expression proceeded caudally in parallel with somite maturation and disappeared in the somites after 2–3 days. SM22α expression in differentiating skeletal muscles in the limb buds was not detected, nor elsewhere in the embryo, indicating that it specifically marks early myotomal muscles.

The expression of SM22α in SMCs was detected in the developing dorsal aorta and the ventricle of the heart, including the trabeculated structure at E9.5. At E10.5, SM22α expression was observed in the umbilical vessels and other forming vessels in the head region. At E12.5, SM22α expression in the basilar artery was very high. The expression of SM22α in visceral SMCs within the gut and bladder, as well as in the bronchi of the lung, which contain a smooth muscle component, became apparent at E13.5. Expression in the cranial vessels and intersomitic arteries was also observed at this stage.

At E14.5, SM22α transcripts were clearly seen in all major vessels, bronchi of the lungs, and guts. There was no signal observed in skeletal muscles or heart. However, expression was detected in the ventral body wall at this stage.

By E17.5, SM22α mRNA was observed in all structures containing SMCs, including the major vessels, and the gut. The signal in the bladder was very intense in all the three layers of smooth muscle, and was not present in the epithelial layer.

Together, the above results demonstrate that SM22α mRNA is expressed in all three muscle types during murine embryogenesis. However, SM22α expression in cardiac and skeletal muscle cells is transient, whereas it is persistent in SMCs. The expression of SM22α in multiple myogenic lineages suggests that aspects of the smooth muscle gene regulatory program may be shared by skeletal and cardiac muscle cells.

The expression pattern of SM22α was clearly distinct from that of SM-MHC, which is not expressed in SMCs until about E10.5, and is never detected in cardiac or skeletal muscle cells (Miano et al, supra)

C. SM α-Actin Expression in Embryonic Tissue

To determine whether SM22α might be expressed in a pattern similar to other smooth muscle genes, the expression pattern of SM22α was compared with that of SM α-actin in the same manner as described above, but using the 3' untranslated region of murine SM α-actin, discussed above, as the SM α-actin anti-sense probe.

Similar to SM22α, SM α-actin mRNA transcripts were first detected in the heart at E8.0. This is consistent with previous studies in chick and rat embryos (Ruzicka et al, *J. Cell. Biol.*, 107:2575–2586 (1988); and Woodcock-Mitchell et al, *Differentiation*, 39:161–166 (1988)). At E8.5, expression was also observed in the aortic sac. Moreover, SM α-actin mRNA transcripts were detected in the dorsal aorta, cranial vessels, and the myotomes of the somites between E9.5 and E10.5. The expression of SM α-actin in the heart gradually decreased after E10.5 and became restricted to the bulbus cordis at E12.5, and at E13.5 it was no longer detectable in the heart.

In contrast to SM22α, SM α-actin expression increased continuously in the myotomes and skeletal muscles after E12.5. At E15.5, the signal was quite intense throughout the head and neck muscles, diaphragm and intercostal muscles.

Thus, the expression patterns of SM22α and SM α-actin overlap extensively during the early stages of differentiation with one notable exception: SM α-actin mRNA persists in skeletal muscle at a time when SM22α is no longer present.

It is not clear why several SMC contractile genes, i.e., SM22α, SM α-actin and calponin, are expressed during cardiogenesis while another, i.e., SM MHC is not. One possibility is that the transcription factors directing SM-MHC expression are distinct from those governing SM α-actin, SM22α and calponin expression. The expression of at least three SMC genes in early embryonic heart suggests that cardiac muscle in early embryogenesis may functionally and structurally resemble smooth muscle. In this regard, it is interesting to note that SM α-actin mRNA has been demonstrated in adult rat hearts subjected to pressure overload (Black et al, *J. Clin. Invest.*, 88:1581–1588 (1991)). Moreover, several cardiac fetal markers are coordinately upregulated in response to pressure overload (Nadal-Ginard et al, *J. Clin. Invest.*, 84:1693–1700 (1989)). This raises the question whether the contractile properties of such perturbed adult cardiomyocytes are functionally comparable to embryonic cardiomyocytes.

EXAMPLE 4

Characterization of the Murine SM22α Gene

As a first step towards identifying regulatory elements for SM22α expression, the structure of the murine SM22α gene from clone SM22α-22 kb/BSKII+ was characterized (FIG. 3).

First, the transcriptional initiation site was determined by a primer extension assay, which was performed as described by Cooper et al, *Nucleic Acids Res.,* 16:8443–8465 (1988).

More specifically, a synthetic oligonucleotide (reverse complement to nucleotides 107–131 of the murine SM22α. cDNA; see FIG. 1):

5'-CAATTTTGGACTGCACTTCTCGGCTC-3' (SEQ ID NO:9) was end-labeled with T4 kinase at 37° C. for 30 min. Without further purification, 2.0 ng of this probe was used by mixing with 25 μg of total RNA in a 20 μl annealing cocktail comprising 300 mM NaCl, 40 mM Tricine (pH 8.0) and 0.1 mM EDTA, and incubated at 65° C. for 10 min, then 48° C. for 2 min, before adding 20 μl of 2×extension buffer comprising 0.2 M Tris-HCl (pH 8.3), 12 mM MgCl, 10 mM DTT, 10 mM dNTP mix and 1.0 μl of Superscript II reverse transcriptase (200 U/μl, BRL) for 1 hr. The reaction was terminated by adding 132 μl of stop cocktail comprising 60 μl of ddH$_2$O, 70 μl of 5.0 M NH$_4$OA$_c$ and 2.0 μl of 0.5 M EDTA. Following ethanol precipitation, the pellet was resuspended in 10 μl of loading buffer (Sequence stop solution, UBS), and heated for 3 min at 95° C. before electrophoresing on a 6.0% (w/v) denaturing polyacrylamide gel. A dideoxy sequencing reaction was loaded in the adjacent lane to determine the precise size of the extended product.

In this manner, 19 additional nucleotides in the 5'-untranslated region, and encoding a portion of the first exon, that were missing from the cDNA were identified in the genomic sequence (SEQ ID NO:6) (FIG. 4). The full-length cDNA sequence, and the deduced open reading frame (SEQ ID NO:2), were deposited on Sep. 19, 1995, at the GenBank Database as accession number U36588, which is incorporated by reference herein.

Next, the intron/exon organization was determined by comparing the sequence of the genomic DNA with the cDNA. As shown in FIG. 3, the SM22α gene was found to span 5.9 kb and contains 5 exons.

To map the transcriptional start site for SM22α, a 360 bp riboprobe that extends from nucleotide +62 to −298 within the second exon (FIG. 3) was used in an RNase protection assay.

A major extended product of 131 bp was detected in RNA from stomach and uterus. No extended product was observed in RNA from liver or yeast, which does not express SM22α. A second smaller extension product was also observed with RNA from stomach and uterus. This may have arisen from premature termination of the primer extension reaction, because RNase protection assays using a genomic fragment extending upstream from exon 1 demonstrated a single major protected species in RNA from stomach that corresponds with the size predicted from primer extension. The length of the extended product indicated that the major initiation site for SM22α transcription is located 76 bp upstream of the first translation codon.

As shown in FIG. 4, there is no consensus TATA box close to the transcription initiation site, but a sequence TTAAA is located at bp −28 that might function as a TATA box.

Two CArG boxes (Gustafson et al, *Mol. Cell. Biol.,* 8:4110–4119 (1988)) are present 150 bp and 274 bp upstream of the transcription initiation site (FIG. 4). CArG boxes have been shown to play an important role in the control of several skeletal and cardiac muscle genes (Satorelli et al, *Genes Dev.,* 4:1811–1822 (1990); Treisman, *Sem. Cancer Biol.,* 1:47–58 (1990); Gustafson et al, *Mol. Cell. Biol.,* 8:4110–4119 (1988); Blank et al, *J. Biol. Chem.,* 267:984–989 (1992)); and French et al, *Mol. Cell. Biol.,* 11:2439–2450 (1991)). The promoter of the SM α-actin gene, which is expressed in a similar pattern as SM22α during development, also contains two CArG elements, which are required for transcriptional activity in cultured SMCs (Shimizu et al, supra; Carroll et al, *Mol. Cell. Biol.,* 8:241–250 (1988); and Blank et al, *J. Biol. Chem.,* 267:984–989 (1992)). Thus, the two CArG boxes in the proximal SM22α promoter may participate in its regulation in myogenic lineages.

EXAMPLE 5

Identification of Cis-regulatory Elements for SM22α

A. Construction of SM22α-Luciferase Reporter Vectors

Figure 5:
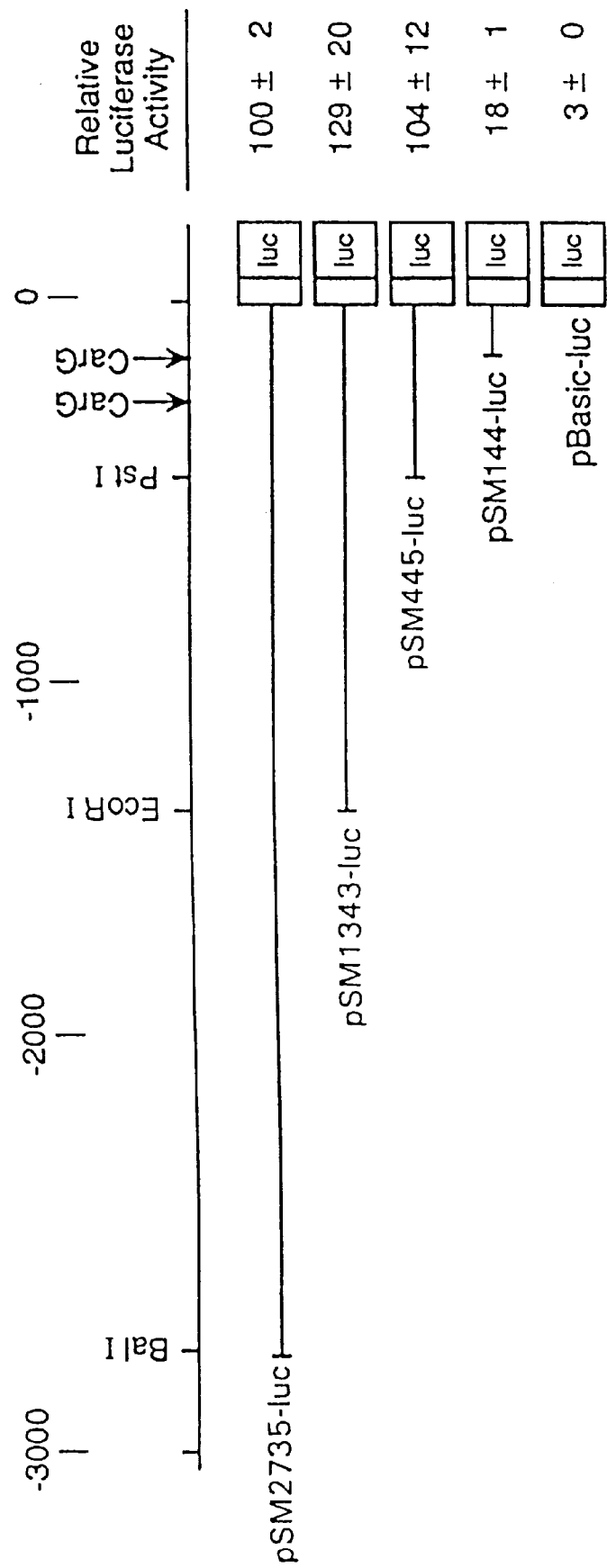
FIG. 5 shows the expression of SM22α-luciferase constructs in cultured cells. DNA fragments extending from nucleotide +62 to the indicated distances upstream of SM22α were tested for transcriptional activity in the luciferase vector. The indicated activities are expressed relative to that of pSM2735-luc.
Figure 6:
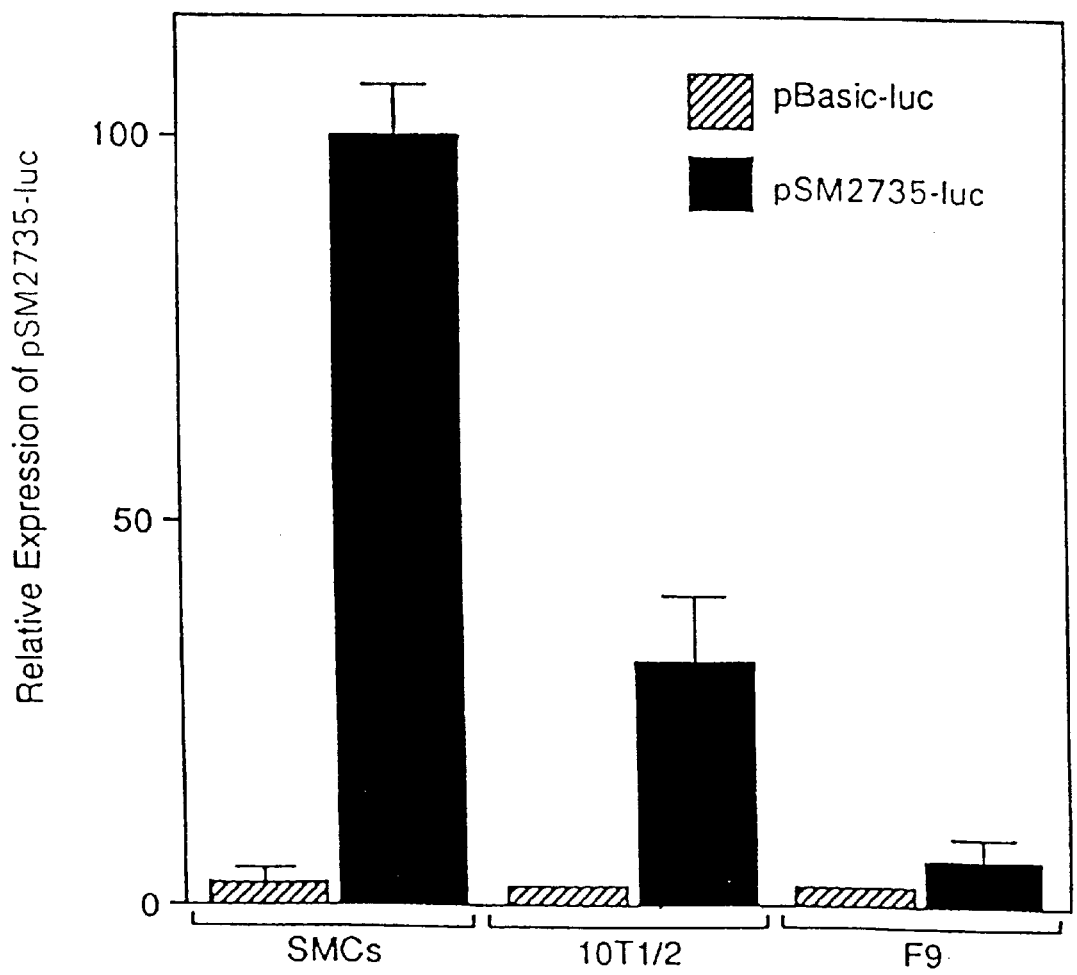
FIG. 6 shows the activities of the SM22α promoter using pSM2735-luc or pBasic-luc transfected F9 cells, 10T1/2 cells and SMCs. The indicated activities were determined using equal amounts of the proteins, and were normalized for transfection efficiency in the cell lines by comparing the activities of pSV2-luc in the cell lines. The results represent the averages of four to six transfection experiments.

As a first step in identifying cis-regulatory elements that may be responsible for SMC-specific expression of SM22α, a series of SM22α-luciferase reporter vectors was created using DNA fragments that extend varying distances upstream from the first exon (FIG. 5).

Initially, a 3892 bp BalI-fragment (SEQ ID NO:3) from SM22α-22 kb/BSKII+ was subcloned into the pBasic-luc vector (Nordeen, *BioTechniques,* 6:454–457 (1988)). This BalI fragment contains 2735 bp of the 5' flanking region, 64 bp of the first exon and 1093 bp of the first intron. The 3892 bp sequence was deposited on Sep. 19, 1995, at the GenBank Database as accession number U36589, which is incorporated by reference herein. To eliminate the intronic sequence, a 2797 bp PCR fragment containing 2735 bp of 5' flanking sequence and the first 62 bp of exon 1 of the SM22α gene was generated using, as primers, the synthetic oligonucleotide 5'-CCAGCTGGTGCCAGGCTTTCGGTGCTAAGGC-3' (SEQ ID NO:10), (the 5' end of this oligonucleotide is located at −2735), and another oligonucleotide, 5'-GACGGCGTCGACGGCTTGGTCGTTTGTGGA-CTGG-3+ (SEQ ID NO:11) (this oligonucleotide is reversed and complementary to sequence +41 to +62 with a SalI site engineered at the 3' end).

The resulting PCR fragment was cloned into the TA vector (Invitrogen), yielding plasmid pSM2735-TA. The insert was then excised by digestion with BamHI and SalI, and the resulting BamHI/SalI fragment (SEQ ID NO:4), corresponding to sequences from −2735 to +62, was subcloned back into pBasic-luc to yield plasmid pSM2735-luc (see FIG. 5).

Next, a 1405 bp EcoRI/SalI fragment (SEQ ID NO:5), and a 507 bp PstI/SalI fragment (SEQ ID NO:6) were excised from the pSM2735-TA construct, and subcloned back into pBasic-luc, resulting in constructs pSM1343-luc and pSM445-luc, respectively (see FIG. 5).

Finally, a fragment containing 144 bp 5' flanking sequence and 62 bp of exon 1 was generated by PCR using the oligonucleotide (SEQ ID NO:11) and a oligonucleotide (SEQ ID NO:12) as primers:

5'-ATGGAGCCTGTGTGGAGTGAGT-3' (SEQ ID NO:12)

The PCR product was then subcloned back into pBasic-luc, resulting in the construct pSM144-luc (see FIG. 5).

The orientations and identities of the inserted fragments in all of these constructs were confirmed by sequencing.

B. Transfection and Luciferase Assays

The above lucifrase reporter constructs were then tested for activity by transient transfection of rat aortic SMCs.

More specifically, rat aortic SMCs, were split and seeded in 6 cm dishes. After 24 hr, the cells were about 70% confluent and ready for transfection. 5.0 μg of each luciferase reporter construct described above, was transfected by calcium phosphate precipitation, as described by Li et al, *Cell,* 71:1181–1194 (1992).

48 hr later, the cells were harvested in 300 μl of 0.1 M Tris-HCl (pH 7.8) containing 1.0 mM DTT. After three cycles of freeze/thaw, the cells were spun for 5 min at 4° C. Aliquots (about 20 μl) of supernatant containing equal quantities of protein were mixed with 330 μl of reaction buffer comprising 0.1 M Tris-HCl (pH 7.8), 5.0 mM ATP, 15 mM MgSO$_4$ and 1.0 mM DTT, and 100 μl of 1.0 mM luciferin (Analytic Luminescence Laboratories; San Diego, Calif.).

All transfections were repeated two to six times. The results are shown in FIG. 5.

As shown in FIG. 5, the reporter construct pSM2735-luc, which extends to −2735 bp, was found to be expressed at a level similar to pSM445-luc, indicating that sequences between −2735 and −445 bp are not required for expression in cultured SMCs. The reporter construct pSM1343-luc was found to be expressed at a slightly higher level than pSM2735-luc, suggesting the possible existence of a negative element between −2735 and −1343 bp. Deletion from −445 to −144 resulted in a dramatic 6-fold decrease in promoter activity, indicating that sequences in this region are important for SM22α transcription. There are two CArG boxes within this region (see FIG. 4) that could be contributing to transcriptional activity.

To determine whether the isolated promoter contained all of the elements required for tissue-specific expression of SM22α, pSM2735-luc and pSM445-luc were also tested in the same manner in 10T1/2 fibroblasts and F9 teratocarcinoma cells, except that the F9 cells were transfected at about 50% confluence. The transfection efficiency of the different cell lines was determined by comparing the expression of pSV$_2$-luc, which contains the SV40 enhancer and promoter. Again, all transfections were repeated two to six times.

The pSM2739-luc reporter construct was expressed at a 3-fold higher level in SMCs than in 10T1/2 cells, and was inactive in F9 cells. This is in agreement with the relative levels of expression of SM22α transcripts in these cell types. The construct pSM445-luc was expressed similarly to pSM2735-luc in the two cell types.

The above results indicate that the proximal promoter of SM22α confers cell-restricted expression in vitro in cultured cells.

EXAMPLE 6

Transgenic Mice

A. Construction of SM22α-lacZ Reporter Constructs

To define the elements required for temporal and spatial expression of SM22α in vivo, two lacZ reporter genes: one that extends from −2735 to +62 bp (pSM2735-lacZ), the other that extends from −2735 to 1093 bp in the first intron (pSM2735/1093-lacZ), were created.

More specifically, a 3892 bp BalI-fragment from SM22α-20 kb/BSKII+ was subcloned into the pBS-lacZ vector (Cheng et al, *J. Cell Biol.,* 119:1649–1656 (1992)) to yield plasmid pSM2735/1093-lacZ. Again, this BalI fragment contains 2735 bp of the 5' flanking region, 64 bp of the first exon and 1093 bp of the first intron. The intronic sequence was eliminated as described above using the oligonucleotide (SEQ ID NO:10) and the oligonucleotide (SEQ ID NO:11).

The resulting PCR fragment was cloned into the TA vector, yielding plasmid pSM2735-TA. The insert was then excised by digestion with BamHI and SalI, and the resulting BamHI/SalI fragment, corresponding to sequences for −2735 to +62, was cloned into pBS-lacZ to yield of plasmid pSM2735-lacZ.

The orientations and identities of the inserted fragments in all of these constructs were confirmed by sequencing.

B. Transfection and β-galactosidase Assays

Transgenic mice were produced using both pSM2735-lacZ and pSM2735/1093-lacZ, and analyzed as described by Cheng et al, supra; and Hogan et al, *Manipulating the Mouse Embryo,* 2nd Ed., Cold Spring Harbor Laboratory Press (1994).

Hybrid inbred (C57BL6×CBA) F1 mice (Jackson Laboratory, Bar Harbor, Me.) were used as stud males, embryo donors, and mature females for breeding. Outbred ICR mice (Harlan Sprague Dawley, Indianapolis, Ind.) were used for vasectomized males and pseudopregnant females.

Stable lines of transgenic mice were maintained by backcrossing to founder animals to nontransgenic (C57BL6× CBAFβ) hybrid mice.

Transgene-positive animals were identified by PCR amplification of tail DNA (Hanley et al, *BioTechniques,* 10:56 (1991)), or by Southern blot analysis.

For histological-analysis, samples were fixed in 2.0% (v/v) paraformaldehyde/0.2% (v/v) glutaraldehyde in PBS at 4° C. for 30 min to 2 hr (depending on sample size). After rinsing in PBS and staining with X-gal, samples were dehydrated with ethanol and cleared in xylene, and embedded in paraffin. For larger samples, 0.1% (w/v) sodium deoxycholate and 0.2% (v/v) NP40 were added to PBS for rinsing and staining process. Embryos were sectioned on a microtome at a thickness of 5–10 μm, and counterstained with hematoxylin and eosin.

To better visualize the vasculature of the embryo, stained embryos were dehydrated in 100% (v/v) methanol for two days, and cleared in a solution of 2 volumes of benzyl benzoate per volume of benzyl alcohol for 1–3 hr before photography.

The resulting transgenic mice, obtained using plasmids pSM-2735/1093-lacZ and pSM-2735-lacZ were initially tested for SM22α promoter activity, and then were examined for lacZ expression as founders and stable transgenic lines.

Both SM22α-lacZ constructs showed comparable expression patterns. That is, transgene expression was detected in the outflow tract and the bulbus cordis of the heart tube at E8.75.

However, the SM22α-lacZ transgene was not expressed in the left ventricle of the heart between E8.75 and E9.5, when endogenous SM22α transcripts were expressed. It has been reported that the atria and ventricles express distinct subsets of contractile proteins and have different conductive and contractile properties (DeHaan, *In: Organogenesis,* Ed., DeHaan et al, New York, Holt, Rinehart and Winston, pages 377–419 (1965)). Several atrial and ventricle lineage-specific markers, such as atrial-specific MHC (Yutzey et al, *Development,* 120:871–883 (1994)), atrial-specific myosin light chain (MLC)-2 (Kubalak et al, *J. Biol. Chem.,* 269:16961–16970 (1994)), and ventrical-specific MLC-2 (O'Brien et al, *Proc. Natl. Acad. Sci., USA,* 90:5157–5161 (1993)), have been identified. However, no markers differentiating left and right ventricles have been previously documented. As discussed above, by in situ hybridization, it was observed in the present invention that SM22α is expressed in both the left and right ventricles of the heart prior to E10.5. It then becomes restricted to the right ventricle at E12.5 and by E13.5, it disappears from the heart. However, in the transgenic mice, this transgene was never expressed in the left ventricle, suggesting that different regulatory elements may be required to direct SM22α expression in the left and right ventricles.

At E9.0, the expression of lacZ in the bulbus cordis and outflow tract increased and expression began to be detected in the dorsal aorta.

At E10.0, lacZ expression increased in the dorsal aorta and structures of the heart including the truncus arteriosus and bulbus cordis. Expression in the somites was barely detectable at E9.5 but became apparent at E10.0.

At E11.5, lacZ expression was evident in the vasculature as well as in the heart and somites. Beginning at E13.5, expression in the heart and somites diminished. LacZ staining marked all of the major vessels in the head and trunk region at this stage. LacZ expression in the vasculature increased continuously through E14.5 and E15.5. During these stages, expression in intercostal vessels could be seen clearly.

At all of the stages examined, the expression of the SM22α-lacZ transgenes paralleled expression of SM22α transcripts in the vascular smooth, cardiac, and skeletal muscle lineages, with no apparent delay between expression of SM22α transcripts and transgene expression. However, during embryogenesis, no lacZ expression was observed in venous, small arteries, and visceral SMCs in structures, such as veins, small arteries, the gut, stomach, and bladder. This suggests that SM22α expression in different types of SMCs is controlled by separable regulatory elements.

There are two major types of SMCs: vascular and visceral. While these SMC types express nearly all of the same muscle-specific genes, they have different contractile and pharmacologic responses and arise from different embryonic progenitors. Moreover, the regulation of SMC gene expression appears to be different in vascular and visceral SMCs, i.e., expression of SM22α in vascular SMCs precedes the expression of SM-MHC (Miano et al, supra), while its expression in visceral SMCs was detected at about the same time as that of SM-MHC. These results, therefore, reveal a previously unrecognized molecular heterogeneity between vascular and visceral SMCs, and suggest that the transcriptional regulatory programs governing muscle gene expression in these two SMC types are distinct.

Thus, the above results demonstrate that SM22α 5'-flanking region is sufficient to direct expression of a lacZ reporter gene in transgenic mice in the vascular smooth, cardiac, and skeletal muscle lineages in a temporospatial pattern similar to that of the endogenous SM22α gene.

The expression pattern of the SM22α-lacZ transgene also allowed visualization of the developing vascular system throughout embryogenesis. LacZ expression was detected in arterial SMCs throughout the developing vessels. Therefore, the isolated SM22α promoter offers an opportunity to genetically manipulate the physiology and pathology of the cardiovascular system by directing genes involved in cell growth and differentiation into the cardiovascular system.

Significant progress has been made toward identifying the transcription factors that control skeletal and cardiac muscle gene expression. However, the mechanisms that regulate SMC-specific gene expression remain largely unknown. Skeletal muscle gene expression is controlled by a family of skeletal muscle-specific basic-Helix-Loop-Helix (bHLH) proteins, MyoD, Myogenin, Myf5 and MRF4, which activate muscle gene expression by binding to the E-box consensus sequence (CANNTG) in the control regions of muscle structural genes (Weintraub et al, supra; and Olson, Dev. Biol., 154:261–272 (1990)). There are no E-boxes in the 445-bp SM22α promoter that directs cell type-restricted expression in vitro, but there are multiple E-boxes in the more distal upstream region that could potentially influence SM22α expression in the somite myotome during embryogenesis.

Interestingly, the promoter of the SM α-actin gene, which is expressed in a similar pattern SM22α in the SMC lineage, contains two CArG elements in nearly the same spatial orientation as those in the SM22α promoter. How SRF might confer SMC-specificity to the SM α-actin promoter remains to be determined. Because SRF is expressed in muscle as well as non-muscle cells, and binds to sequences in the promoters of many skeletal and cardiac muscle genes, as well as growth factor-responsive genes, it is likely that it acts combinatorially with other factors to control SMC gene expression.

GATA-4, is a cardiac transcription factor that has been shown to confer the cardiac-specific expression of the α-MHC promoter (Molkentin et al, Mol. Cell. Biol., 14:4947–4957 (1994)). There are no GATA-4 consensus binding sites in the 445-bp SM22α promoter. Further analysis of this and other constructs in vivo should provide a clear picture as to the required elements for cardiac muscle expression of SM22α.

SM22α is one of the only SMC markers that is not down-regulated during the course of vascular occlusive disease. Thus, this promoter should be active in all SMCs of the vessel wall. This is important because other SMC promoters which are currently under investigation for similar gene therapy applications, may not be as efficacious, since their endogenous gene is often down-regulated in vascular lesions.

The specific expression of the SM22α promoter in vivo demonstrated for the first time in the present invention makes this promoter a useful tool for directing SMC-specific expression within the vessel wall in gene therapy. Thus, the isolated SM22α promoter described herein is believed to be useful for treating vascular diseases, especially restenosis following balloon angioplasty.

While the invention has been described in detail, and with reference to specific embodiments thereof, it will be apparent to one of ordinary skill in the art that various changes and modifications can be made therein without departing from the spirit and scope thereof.

---

What is claimed:

1. A method for expression of foreign DNA in mammalian arterial smooth muscle cell, comprising: introducing into mammalian arterial smooth muscle cells a gene transfer vector comprising a mouse SM22α promoter operably linked to foreign DNA encoding a desired polypeptide or RNA, wherein said foreign DNA is expressed, and wherein said promoter is selected from the group consisting of SEQ ID NO:3, SEQ ID NO:4, SEQ ID NO:5 and SEQ ID NO:6.

2. The method of claim 1, wherein said polypeptide is selected from the group consisting of basic fibroblast growth factor 1 receptor dominant negative mutant, p21, angiopeptin, endothelial cell nitric oxide synthase, and non-phosphorylated Rb.

3. The method of claim 1, wherein said RNA is selected from the group consisting of anti-sense c-myc RNA and anti-sense c-myb RNA.

4. The method of claim 1, wherein said vector encodes and expresses a reporter molecule.

5. The method of claim 4, wherein said reporter molecule is selected from the group consisting of β-galactosidase, luciferase and chloramphenicol acetyltransferase.

6. The method of claim 1, wherein said introducing is carried out by a means selected from the group consisting of adenovirus infection, liposome-mediated transfer and microinjection.

* * * * *

UNITED STATES PATENT AND TRADEMARK OFFICE
CERTIFICATE OF CORRECTION

PATENT NO. : 6,015,711
DATED : January 18, 2000
INVENTOR(S) :
Eric N. OLSON, Li LI It is certified that error appears in the above-identified patent and that said Letters Patent is hereby corrected as shown below:

Column 6, line 57, delete "no".

Column 12, line 38, change "3+" to --3'--.

Column 14, line 21, change "CBAFβ" to -- CBAF1--.

Signed and Sealed this

Seventeenth Day of April, 2001

*Attest:*

NICHOLAS P. GODICI

*Attesting Officer*     *Acting Director of the United States Patent and Trademark Office*

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
        (A) LENGTH: 1078 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO:1:

```
GACACCGAAG CTACTCTCCT TCCAGTCCAC AAACGACCAA GCCTTCTCTG CCTCAACATG     60
GCCAACAAGG GTCCATCCTA CGGCATGAGC CGAGAAGTGC AGTCCAAAAT TGAGAAGAAG    120
TATGACGAGG AGCTGGAGGA GCGACTAGTG GAGTGGATTG TAGTGCAGTG TGGCCCTGAT    180
GTAGGCCGCC CAGATCGTGG GCGCCTGGGC TTCCAGGTGT GGCTGAAGAA TGGTGTGATT    240
CTGAGCAAAT TGGTGAACAG CCTGTATCCT GAGGGATCGA AGCCAGTGAA GGTGCCTGAG    300
AACCCACCCT CCATGGTCTT TAAGCAGATG GAACAGGTGG CTCAATTCTT GAAGGCAGCT    360
GAAGATTATG GAGTCATCAA GACTGACATG TTCCAGACTG TTGACCTCTA TGAAGGTAAG    420
GATATGGCAG CAGTGCAGAG GACTCTAATG GCTTTGGGCA GTTTGGCTGT GACCAAAAAC    480
GATGGAAACT ACCGTGGAGA TCCCAACTGG TTTATGAAGA AAGCCCAGGA GCATAAGAGG    540
GACTTCACAG ACAGCCAACT GCAGGAGGGG AAGCACGTCA TTGGCCTTCA AATGGGCAGC    600
AACAGAGGAG CCTCGCAGGC TGGCATGACA GGCTATGGGC GACCCCGGCA GATCATCAGT    660
TAGAAAGGGA AGGCCAGCCC TGAGCTGCAG CATCCTGCTT AGCCTGCCTC ACAAATGCCT    720
ATGTAGGTTC TTAGCCCTGA CAGCTCTGAG GTGTCACTGG GCAAAGATGA CTGCACATGG    780
GCAGCTCCCA CCTATCCTTA GCCTCAGCCC AGCATCTTAC CCCAGAGCCA CCACTGCCCT    840
GGCCCCTGTT CCCAAGCTGT ACCCCCACCT CTACTGTTCC TCTCATCCTG GAGTAAGCAG    900
GGAGAAGTGG GCTGGGGTAG CCTGCTGTAG GCCAGCCCAC TGTCCTTGAT ATCGAATGTC    960
CTTTGAAGGA GACCCAGCCC AGCCTCTACA TCTTTTCCTG GAATATGTTT TTGGGTTGAA   1020
ATTCAAAAAG GAAAAAAGCA AAATATATAA ATATATATAT AAAAAAAAAA AAAAAAA     1078
```

(2) INFORMATION FOR SEQ ID NO:2:

(i) SEQUENCE CHARACTERISTICS:
        (A) LENGTH: 201 amino acids
        (B) TYPE: amino acid
        (D) TOPOLOGY: linear (ii) MOLECULE TYPE: protein (iii) HYPOTHETICAL: YES (xi) SEQUENCE DESCRIPTION: SEQ ID NO:2:

```
Met Ala Asn Lys Gly Pro Ser Tyr Gly Met Ser Arg Glu Val Gln Ser Lys
1               5                   10                  15

Ile Glu Lys Lys Tyr Asp Glu Glu Leu Glu Arg Leu Val Glu Trp Ile
            20                  25                  30

Val Val Gln Cys Gly Pro Asp Val Gly Arg Pro Asp Arg Gly Arg Leu Gly
35                  40                  45                  50

Phe Gln Val Trp Leu Lys Asn Gly Val Ile Leu Ser Lys Leu Val Asn Ser
            55                  60                  65

Leu Tyr Pro Glu Gly Ser Lys Pro Val Lys Val Pro Glu Asn Pro Pro Ser
70                  75                  80                  85
```

```
Met Val Phe Lys Gln Met Glu Gln Val Ala Gln Phe Leu Lys Ala Ala Glu
             90                  95                 100

Asp Tyr Gly Val Ile Lys Thr Asp Met Phe Gln Thr Val Asp Leu Tyr Glu
            105                 110                 115

Gly Lys Asp Met Ala Ala Val Gln Arg Thr Leu Met Ala Lys Gly Ser Leu
120                 125                 130                 135

Ala Val Thr Lys Asn Asp Gly Asn Tyr Arg Gly Asp Pro Asn Trp Phe Met
            140                 145                 150

Lys Lys Ala Gln Glu His Lys Arg Asp Phe Thr Asp Ser Gln Leu Gln Glu
155                 160                 165                 170

Gly Lys His Val Ile Gly Leu Gln Met Gly Ser Asn Arg Gly Ala Ser Gln
            175                 180                 185

Ala Gly Met Thr Gly Tyr Gly Arg Pro Arg Gln Ile Ile Ser
190                 195                 200
```

(2) INFORMATION FOR SEQ ID NO:3:

(i) SEQUENCE CHARACTERISTICS:
        (A) LENGTH: 3892 base pairs
        (B) TYPE: nucleic acid
        (C) STRANDEDNESS: single
        (D) TOPOLOGY: linear (ii) MOLECULE TYPE: genomic (iii) HYPOTHETICAL: NO (xi) SEQUENCE DESCRIPTION: SEQ ID NO:3:

```
CCAGCTGGTG CCAGGCTTTC GGTGCTAAGG CCTGAAAGGG GACTAGGTAC GACCCTCCTC      60

CCTGACCTGT GCTTGGAGCT GGCTCTTCAG CAGTGAGGGC CAGCCCAAGT TGAGTCTTCT     120

GATCGGGGAC TGAATTCAGA GGCCACCTCA TCCCACCAGC CACTAGAATG ATGCCAGCAC     180

TAGGGTTGGT GGGAAGTGGC AACTCACTGT CCCCTTCCAC ACCCTCAGTC CTGCCAAGCC     240

CCAGATGGGG GGCTCTCAGT GCCATTGACA CTGCCCAAGA ATGTCTAGAG GCCACGGAAC     300

GGTGCCAGCA CACAGTCCCT TTTGCCTCTT TCACGGGAGC AGGAGTCCCA GTGCCTGTCG     360

TGGAAAGGGA GGAACATGCC AGGTCCCTGT GTGTCCTTGG CCCTGTCTCA CCAAAGGACT     420

CAGGGCTGGT TTCTGAGTTT CCGTCCAGTA TTTAGCCAAG TTCTGTGTTA GTCACGTAGG     480

CCTAAGAGCC TTGGCGTTTA CAGAGTCACC CAGCTCCAGG CCCCTGGCCA CTTTGGTACT     540

TGGTTGCCCC TCACTCCACC AGGTCCATTC CAGATGCCAA GAGTGGGCCC CAGGAATGTG     600

TTTCCTTCTC TCCACCATGT TTTTATAGCT CTTGGGCTGG GAGAAGAGGC GGGTCTGGGT     660

CTTTGTTTCT GAGCTTTGTT CTATGTTCCT CCATGCTACG GTTGCAATTG TTTTCTATGA     720

ACGAGTACAT TCAATAAAGA CAACCAGACC TGGGATTTGG GGTCTTACTG ATGTGTTGGG     780

AGGTGCAGGA GCCTCCGTGT CCCATTTATT TTGGGCCTTC CCGTCTCGTT TCTGTGCGTG     840

GCTACATTGG GAATGACCTT CCTTGATCCC ACCAAGCCAC CCATTGATTC TGTAAACATG     900

TGACCCTTGC TCCAAGCATT GCTTACAGGA GCAGGATACT GAAAGTGTGT CTGTGCCCTC     960

TCCTGATAAC CCCTCCCTTC AGCAGGCACA CAGCACCTGA CTACCCACCA CGTATGTAAA    1020

CGTCAGTATC TTTTCCAGTC AGCTCGGCAG ATGGGTGTCC AGGCTGTGCC ATGATGCACC    1080

TCAAGTGGGC AGAGCCCTTG CAGGCCAAGG TTTTAAAGGC TGTTCAGGAA TGGATGGCAA    1140

GCAGGATCTA AGAGGAGGGG GGGTTGTTGT TGTTTGGGGG GGGGTGGTT TTGGTTTGTT    1200

TTTTTTGAGA CAGGGTTTTC TCTGTGTGGC CCTGGCCCTC CTGGAACCCA CTCTGTAGAC    1260

CAGGCTGGCC TTGAACTCAG AAATCTGCCT GCCTCTGCCT CCCGAGTGCT GGGATTAAAG    1320
```

```
GCGTGTGCCC ATCGAGGAGG GAGATTTTAT TTAGATTATA AAAAGGGCGG GATTTGGGGA      1380

ATCCTGTCTA GTGAATTCAG GACGTAATCA GTGGCTGGAA AGCAAGAGCT CTAGAGGAGC      1440

TCCAGCTTAT TATGACCCTT CCTTCAGATG CCACAAGGAG GTGCTGGAGT TCTATGCACC      1500

AATAGCTTAA ACCAGCCAGG CTGGCTGTAG TGGATTGAGC GTCTGAGGCT GCACCTCTCT      1560

GGCCTGCAGC CAGTTCCTGG GTGAGACTGA CCCTGCCTGA GGGTTCTCTC CTTCCCTCTC      1620

TCTACTCCTT TCCTCCCTCT CCCTCTCCCT CTCTCTGTTT CCTGAGGTTT CCAGGATTGG      1680

GGATGGGACT CAGAGACACC ACTAAAGCCT TACCTTTTAA GAAGTTGCAT TCAGTGAGTG      1740

TGTGAGACAT AGCACAGATA GGGGCAGAGG AGAGCTGGTT CTGTCTCCAC TGTGTTTGGT      1800

CTTGGGTACT GAACTCAGAC CATCAGGTGT GATAGCAGTT GTCTTTAACC CTAACCCTGA      1860

GCCTGTCTCA CCTGTCCCTT CCCAAGACCA CTGAAGCTAG GTGCAAGATA AGTGGGGACC      1920

CTTTCTGAGG TGGTAGGATC TTTCACGATA AGGACTATTT TGAAGGGAGG GAGGGTGACA      1980

CTGTCCTAGT CCTCTTACCC TAGTGTCCTC CAGCCTTGCC AGGCCTTAAA CATCCGCCCA      2040

TTGTCACCGC TCTAGAAGGG GCCAGGGTTG ACTTGCTGCT AAACAAGGCA CTCCCTAGAG      2100

AAGCACCCGC TAGAAGCATA CCATACCTGT GGGCAGGATG ACCCATGTTC TGCCACGCAC      2160

TTGGTAGCCT TGGAAAGGCC ACTTTGAACC TCAATTTTCT CAACTGTTAA ATGGGGTGGT      2220

AACTGCTATC TCATAATAAA GGGGAACGTG AAAGGAAGGC GTTTGCATAG TGCCTGGTTG      2280

TGCAGCCAGG CTGCAGTCAA GACTAGTTCC CACCAACTCG ATTTTAAAGC CTTGCAAGAA      2340

GGTGGCTTGT TTGTCCCTTG CAGGTTCCTT TGTCGGCCA AACTCTAGAA TGCCTCCCCC       2400

TTTCTTTCTC ATTGAAGAGC AGACCCAAGT CCGGGTAACA AGGAAGGGTT TCAGGGTCCT      2460

GCCCATAAAA GGTTTTTCCC GGCCGCCCTC AGCACCGCCC CGCCCCGACC CCCGCAGCAT      2520

CTCCAAAGCA TGCAGAGAAT GTCTCCGGCT GCCCCCGACA GACTGCTCCA ACTTGGTGTC      2580

TTTCCCCAAA TATGGAGCCT GTGTGGAGTG AGTGGGGCGG CCCGGGGTGG TGAGCCAAGC      2640

AGACTTCCAT GGGCAGGGAG GGGCGCCAGC GGACGGCAGA GGGGTGACAT CACTGCCTAG      2700

GCGGCCTTTA AACCCCTCAC CCAGCCGGCG CCCCAGCCCG TCTGCCCCAG CCCAGACACC      2760

GAAGCTACTC TCCTTCCAGT CCACAAACGA CCAAGCCTTG TAAGTGCAAG TCATGGGAGC      2820

AGAAGGGCTG TGGCCTCAGA TAGATCCCCT AGTCTCTTCT AGTTTGGTGG GTGGAATTGG      2880

GTCCCTAGAG ACCATCCTCT GTGTTAGACA AAAAGTCTGG GTTAAAATGC CTAGGATGAT      2940

TGGACTGGGG AAAAAGACTA AATGGGAAAG TTACTAGGGT GAGAGGGAGG CTCAATTTTC      3000

AGTCACTGCC CCACCCATAG GTGTATGGGC TATGTGTTAG GCCCAAAGAG GTGACAAATG      3060

AGGCCAAGGG AACAACTCCA TCTTTGGATC TCCAAGAAGG TGAGGGGCTA AGTCCTGGAA      3120

AGCAGTGACC CACTGATGGT CCCCAGGGCT AATGCAACTC GGGGGAGCCA GGAGGTAGCC      3180

CCCTCAGGCA GTGGAGGACT AAAGATCTTA TTGGTTGGTA GCCCTAGGGA TCCAAACCCC      3240

AGGGCGCTAT GTGTGGAAGG CATGTGCTCC ATCTACCACA GAAGTTTAAT GCTTCAGACT      3300

AGCCTGGGAT AGGGCCTGCT TTTTCTTTCC TTTTCTCTCT CTCTCTCTCT CTCTCTCTCT      3360

CTCTCTCTCT CTCTCTCTCT CTCTCTCTTT CTTTCCTTTT CTCTCTTTCA CTCTCTCTTT      3420

CTAATTTTCT TTCTCTTTTT TTCTTTCTTT TCTTTAGACA GGGTTCCCTC TGTGTAGCCC      3480

TGGCTGTTCT GGAACTCACT CTTTAGACCA GGCTGGCCTC GAACTCAGAA ATCTACCTGC      3540

CTCTGCCTCC CAAGTGCTGG GATTAAAGGC GTGTGCCACC ACTGCCCAGC TAAGGTTTGC      3600

TTTTTCATGA CAGCTTGGTC CAGTTTGAGA GTAGGAGGTC AGTCCACTGT AGGCAGATAG      3660

GTGACAGGTG GCAGATAGGT GACAGATAGG TGACAGGTGG AGGAGCTTTG GAACTGGGAC      3720
```

```
TGGACAGCCC TGGGACCCCT GTTCCTCCCA AAGGGTCTTG GTGGTTCCCC CTTGGGCTC     3780

TCTAAAGGAT GTCAGTGGGC TGTTGCCACA TCTATATAAG AGGACTAGTC TTCTGGAATT    3840

TAGGTGTGAT CTCTCAGGGA TGCAGAAATG CTCACCCTTA CTGTCATTTT AT            3892
```

(2) INFORMATION FOR SEQ ID NO:4:

(i) SEQUENCE CHARACTERISTICS:
        (A) LENGTH: 2797 base pairs
        (B) TYPE: nucleic acid
        (C) STRANDEDNESS: single
        (D) TOPOLOGY: linear (ii) MOLECULE TYPE: genomic (iii) HYPOTHETICAL: NO (xi) SEQUENCE DESCRIPTION: SEQ ID NO:4:

```
CCAGCTGGTG CCAGGCTTTC GGTGCTAAGG CCTGAAAGGG GACTAGGTAC GACCCTCCTC      60

CCTGACCTGT GCTTGGAGCT GGCTCTTCAG CAGTGAGGGC CAGCCCAAGT TGAGTCTTCT     120

GATCGGGGAC TGAATTCAGA GGCCACCTCA TCCCACCAGC CACTAGAATG ATGCCAGCAC     180

TAGGGTTGGT GGGAAGTGGC AACTCACTGT CCCCTTCCAC ACCCTCAGTC CTGCCAAGCC     240

CCAGATGGGG GGCTCTCAGT GCCATTGACA CTGCCCAAGA ATGTCTAGAG GCCACGGAAC     300

GGTGCCAGCA CACAGTCCCT TTTGCCTCTT TCACGGGAGC AGGAGTCCCA GTGCCTGTCG     360

TGGAAAGGGA GGAACATGCC AGGTCCCTGT GTGTCCTTGG CCCTGTCTCA CCAAAGGACT     420

CAGGGCTGGT TTCTGAGTTT CCGTCCAGTA TTTAGCCAAG TTCTGTGTTA GTCACGTAGG     480

CCTAAGAGCC TTGGCGTTTA CAGAGTCACC CAGCTCCAGG CCCCTGGCCA CTTTGGTACT     540

TGGTTGCCCC TCACTCCACC AGGTCCATTC CAGATGCCAA GAGTGGGCCC CAGGAATGTG     600

TTTCCTTCTC TCCACCATGT TTTTATAGCT CTTGGGCTGG GAGAAGAGGC GGGTCTGGGT     660

CTTTGTTTCT GAGCTTTGTT CTATGTTCCT CCATGCTACG GTTGCAATTG TTTTCTATGA     720

ACGAGTACAT TCAATAAAGA CAACCAGACC TGGGATTTGG GGTCTTACTG ATGTGTTGGG     780

AGGTGCAGGA GCCTCCGTGT CCCATTTATT TTGGGCCTTC CCGTCTCGTT TCTGTGCGTG     840

GCTACATTGG GAATGACCTT CCTTGATCCC ACCAAGCCAC CCATTGATTC TGTAAACATG     900

TGACCCTTGC TCCAAGCATT GCTTACAGGA GCAGGATACT GAAAGTGTGT CTGTGCCCTC     960

TCCTGATAAC CCCTCCCTTC AGCAGGCACA CAGCACCTGA CTACCCACCA CGTATGTAAA    1020

CGTCAGTATC TTTTCCAGTC AGCTCGGCAG ATGGGTGTCC AGGCTGTGCC ATGATGCACC    1080

TCAAGTGGGC AGAGCCCTTG CAGGCCAAGG TTTTAAAGGC TGTTCAGGAA TGGATGGCAA    1140

GCAGGATCTA AGAGGAGGGG GGGTTGTTGT TGTTTGGGGG GGGGTGGTT TTGGTTTGTT     1200

TTTTTTGAGA CAGGGTTTTC TCTGTGTGGC CCTGGCCCTC CTGGAACCCA CTCTGTAGAC    1260

CAGGCTGGCC TTGAACTCAG AAATCTGCCT GCCTCTGCCT CCCGAGTGCT GGGATTAAAG    1320

GCGTGTGCCC ATCGAGGAGG GAGATTTTAT TTAGATTATA AAAGGGCGG GATTTGGGGA     1380

ATCCTGTCTA GTGAATTCAG GACGTAATCA GTGGCTGGAA AGCAAGAGCT CTAGAGGAGC    1440

TCCAGCTTAT TATGACCCTT CCTTCAGATG CCACAAGGAG GTGCTGGAGT TCTATGCACC    1500

AATAGCTTAA ACCAGCCAGG CTGGCTGTAG TGGATTGAGC GTCTGAGGCT GCACCTCTCT    1560

GGCCTGCAGC CAGTTCCTGG GTGAGACTGA CCCTGCCTGA GGGTTCTCTC CTTCCCTCTC    1620

TCTACTCCTT TCCTCCCTCT CCCTCTCCCT CTCTCTGTTT CCTGAGGTTT CCAGGATTGG    1680

GGATGGGACT CAGAGACACC ACTAAAGCCT TACCTTTTAA GAAGTTGCAT TCAGTGAGTG    1740

TGTGAGACAT AGCACAGATA GGGGCAGAGG AGAGCTGGTT CTGTCTCCAC TGTGTTTGGT    1800
```

```
CTTGGGTACT GAACTCAGAC CATCAGGTGT GATAGCAGTT GTCTTTAACC CTAACCCTGA      1860

GCCTGTCTCA CCTGTCCCTT CCCAAGACCA CTGAAGCTAG GTGCAAGATA AGTGGGGACC      1920

CTTTCTGAGG TGGTAGGATC TTTCACGATA AGGACTATTT TGAAGGGAGG GAGGGTGACA      1980

CTGTCCTAGT CCTCTTACCC TAGTGTCCTC CAGCCTTGCC AGGCCTTAAA CATCCGCCCA      2040

TTGTCACCGC TCTAGAAGGG GCCAGGGTTG ACTTGCTGCT AAACAAGGCA CTCCCTAGAG      2100

AAGCACCCGC TAGAAGCATA CCATACCTGT GGGCAGGATG ACCCATGTTC TGCCACGCAC      2160

TTGGTAGCCT TGGAAAGGCC ACTTTGAACC TCAATTTTCT CAACTGTTAA ATGGGGTGGT      2220

AACTGCTATC TCATAATAAA GGGGAACGTG AAAGGAAGGC GTTTGCATAG TGCCTGGTTG      2280

TGCAGCCAGG CTGCAGTCAA GACTAGTTCC CACCAACTCG ATTTTAAAGC CTTGCAAGAA      2340

GGTGGCTTGT TTGTCCCTTG CAGGTTCCTT TGTCGGGCCA AACTCTAGAA TGCCTCCCCC      2400

TTTCTTTCTC ATTGAAGAGC AGACCCAAGT CCGGGTAACA AGGAAGGGTT TCAGGGTCCT      2460

GCCCATAAAA GGTTTTTCCC GGCCGCCCTC AGCACCGCCC CGCCCCGACC CCCGCAGCAT      2520

CTCCAAAGCA TGCAGAGAAT GTCTCCGGCT GCCCCCGACA GACTGCTCCA ACTTGGTGTC      2580

TTTCCCCAAA TATGGAGCCT GTGTGGAGTG AGTGGGCGG CCCGGGGTGG TGAGCCAAGC       2640

AGACTTCCAT GGGCAGGGAG GGGCGCCAGC GGACGGCAGA GGGGTGACAT CACTGCCTAG      2700

GCGGCCTTTA AACCCCTCAC CCAGCCGGCG CCCCAGCCCG TCTGCCCCAG CCCAGACACC      2760

GAAGCTACTC TCCTTCCAGT CCACAAACGA CCAAGCC                              2797
```

(2) INFORMATION FOR SEQ ID NO:5:

(i) SEQUENCE CHARACTERISTICS:
        (A) LENGTH: 1405 base pairs
        (B) TYPE: nucleic acid
        (C) STRANDEDNESS: single
        (D) TOPOLOGY: linear (ii) MOLECULE TYPE: genomic (iii) HYPOTHETICAL: NO (xi) SEQUENCE DESCRIPTION: SEQ ID NO:5:

```
GAATTCAGGA CGTAATCAGT GGCTGGAAAG CAAGAGCTCT AGAGGAGCTC CAGCTTATTA       60

TGACCCTTCC TTCAGATGCC ACAAGGAGGT GCTGGAGTTC TATGCACCAA TAGCTTAAAC      120

CAGCCAGGCT GGCTGTAGTG GATTGAGCGT CTGAGGCTGC ACCTCTCTGG CCTGCAGCCA      180

GTTCCTGGGT GAGACTGACC CTGCCTGAGG GTTCTCTCCT TCCCTCTCTC TACTCCTTTC      240

CTCCCTCTCC CTCTCCCTCT CTCTGTTTCC TGAGGTTTCC AGGATTGGGG ATGGGACTCA      300

GAGACACCAC TAAAGCCTTA CCTTTTAAGA AGTTGCATTC AGTGAGTGTG TGAGACATAG      360

CACAGATAGG GGCAGAGGAG AGCTGGTTCT GTCTCCACTG TGTTTGGTCT TGGGTACTGA      420

ACTCAGACCA TCAGGTGTGA TAGCAGTTGT CTTTAACCCT AACCCTGAGC CTGTCTCACC      480

TGTCCCTTCC CAAGACCACT GAAGCTAGGT GCAAGATAAG TGGGACCCT TTCTGAGGTG       540

GTAGGATCTT TCACGATAAG GACTATTTTG AAGGGAGGGA GGGTGACACT GTCCTAGTCC      600

TCTTACCCTA GTGTCCTCCA GCCTTGCCAG GCCTTAAACA TCCGCCCATT GTCACCGCTC      660

TAGAAGGGGC CAGGGTTGAC TTGCTGCTAA ACAAGGCACT CCCTAGAGAA GCACCCGCTA      720

GAAGCATACC ATACCTGTGG GCAGGATGAC CCATGTTCTG CCACGCACTT GGTAGCCTTG      780

GAAAGGCCAC TTTGAACCTC AATTTTCTCA ACTGTTAAAT GGGGTGGTAA CTGCTATCTC      840

ATAATAAAGG GGAACGTGAA AGGAAGGCGT TTGCATAGTG CCTGGTTGTG CAGCCAGGCT      900
```

```
GCAGTCAAGA CTAGTTCCCA CCAACTCGAT TTTAAAGCCT TGCAAGAAGG TGGCTTGTTT      960

GTCCCTTGCA GGTTCCTTTG TCGGGCCAAA CTCTAGAATG CCTCCCCCTT TCTTTCTCAT     1020

TGAAGAGCAG ACCCAAGTCC GGGTAACAAG GAAGGGTTTC AGGGTCCTGC CCATAAAAGG     1080

TTTTTCCCGG CCGCCCTCAG CACCGCCCCG CCCCGACCCC CGCAGCATCT CCAAAGCATG     1140

CAGAGAATGT CTCCGGCTGC CCCCGACAGA CTGCTCCAAC TTGGTGTCTT TCCCCAAATA     1200

TGGAGCCTGT GTGGAGTGAG TGGGGCGGCC CGGGGTGGTG AGCCAAGCAG ACTTCCATGG     1260

GCAGGGAGGG GCGCCAGCGG ACGGCAGAGG GGTGACATCA CTGCCTAGGC GGCCTTTAAA     1320

CCCCTCACCC AGCCGGCGCC CCAGCCCGTC TGCCCCAGCC CAGACACCGA AGCTACTCTC     1380

CTTCCAGTCC ACAAACGACC AAGCC                                          1405

(2) INFORMATION FOR SEQ ID NO:6:

(i) SEQUENCE CHARACTERISTICS:
        (A) LENGTH: 507 base pairs
        (B) TYPE: nucleic acid
        (C) STRANDEDNESS: single
        (D) TOPOLOGY: linear (ii) MOLECULE TYPE: genomic (iii) HYPOTHETICAL: NO (xi) SEQUENCE DESCRIPTION: SEQ ID NO:6:

CTGCAGTCAA GACTAGTTCC CACCAACTCG ATTTTAAAGC CTTGCAAGAA GGTGGCTTGT       60

TTGTCCCTTG CAGGTTCCTT TGTCGGGCCA AACTCTAGAA TGCCTCCCCC TTTCTTTCTC      120

ATTGAAGAGC AGACCCAAGT CCGGGTAACA AGGAAGGGTT TCAGGGTCCT GCCCATAAAA      180

GGTTTTTCCC GGCCGCCCTC AGCACCGCCC CGCCCCGACC CCCGCAGCAT CTCCAAAGCA      240

TGCAGAGAAT GTCTCCGGCT GCCCCCGACA GACTGCTCCA ACTTGGTGTC TTTCCCCAAA      300

TATGGAGCCT GTGTGGAGTG AGTGGGGCGG CCCGGGGTGG TGAGCCAAGC AGACTTCCAT      360

GGGCAGGGAG GGGCGCCAGC GGACGGCAGA GGGGTGACAT CACTGCCTAG GCGGCCTTTA      420

AACCCCTCAC CCAGCCGGCG CCCCAGCCCG TCTGCCCCAG CCCAGACACC GAAGCTACTC      480

TCCTTCCAGT CCACAAACGA CCAAGCC                                         507

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: synthetic (iii) HYPOTHETICAL: NO (xi) SEQUENCE DESCRIPTION: SEQ ID NO:7:

ATGGCCAACA AGGGTCCATC C                                                21

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: synthetic (iii) HYPOTHETICAL: NO
```

-continued (xi) SEQUENCE DESCRIPTION: SEQ ID NO:8:

TCCATCTGCT TGAAGACCAT G							21

(2) INFORMATION FOR SEQ ID NO:9:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: synthetic (iii) HYPOTHETICAL: NO (xi) SEQUENCE DESCRIPTION: SEQ ID NO:9:

CAATTTTGGA CTGCACTTCT CGGCTC		26

(2) INFORMATION FOR SEQ ID NO:10:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: synthetic (iii) HYPOTHETICAL: NO (xi) SEQUENCE DESCRIPTION: SEQ ID NO:10:

CCAGCTGGTG CCAGGCTTTC GGTGCTAAGG C		31

(2) INFORMATION FOR SEQ ID NO:11:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: synthetic (iii) HYPOTHETICAL: NO (xi) SEQUENCE DESCRIPTION: SEQ ID NO:11:

GACGGCGTCG ACGGCTTGGT CGTTTGTGGA CTGG		34

(2) INFORMATION FOR SEQ ID NO:12:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: synthetic (iii) HYPOTHETICAL: NO (xi) SEQUENCE DESCRIPTION: SEQ ID NO:12:

ATGGAGCCTG TGTGGAGTGA GT		22